(12) United States Patent
Shin et al.

(10) Patent No.: US 12,366,670 B2
(45) Date of Patent: Jul. 22, 2025

(54) DEVICE FOR DETECTING THERAPEUTIC RADIATION BASED ON OPTICAL DISK WITH SOLAR CELLS

(71) Applicants: NATIONAL CANCER CENTER, Goyang-si (KR); SEOUL NATIONAL UNIVERSITY HOSPITAL, Seoul (KR)

(72) Inventors: Dongho Shin, Suwon-si (KR); Tae Hyun Kim, Seoul (KR); Tae-Ho Kim, Goyang-si (KR); Haksoo Kim, Goyang-si (KR); Dong-Seok Shin, Incheon (KR); Se Byeong Lee, Goyang-si (KR); Youngkyung Lim, Paju-si (KR); Jonghwi Jeong, Seoul (KR); Jaeman Son, Seoul (KR)

(73) Assignees: NATIONAL CANCER CENTER, Goyang-si (KR); SEOUL NATIONAL UNIVERSITY HOSPITAL, Seoul (KR)

( * ) Notice: Subject to any disclaimer, the term of this patent is extended or adjusted under 35 U.S.C. 154(b) by 222 days.

(21) Appl. No.: 18/181,660

(22) Filed: Mar. 10, 2023

(65) Prior Publication Data
US 2023/0288582 A1 Sep. 14, 2023

(30) Foreign Application Priority Data
Mar. 11, 2022 (KR) ........................ 10-2022-0030870

(51) Int. Cl.
*A61N 5/10* (2006.01)
*G01T 1/20* (2006.01)
(Continued)

(52) U.S. Cl.
CPC .......... *G01T 1/2018* (2013.01); *A61N 5/1048* (2013.01); *H01J 37/244* (2013.01);
(Continued)

(58) Field of Classification Search
CPC .......... G01T 1/2018; G01T 1/29; G01T 1/02; G01T 1/161; A61N 5/1048;
(Continued)

(56) References Cited

U.S. PATENT DOCUMENTS

| 2008/0061245 A1* | 3/2008 | Yamamoto ................ G01T 1/02 250/374 |
| 2012/0168630 A1* | 7/2012 | Beddar .................... G01T 1/204 250/362 |

(Continued)

FOREIGN PATENT DOCUMENTS

KR  10-2015-0079239 A  7/2015

OTHER PUBLICATIONS

Korean Office Action issued Feb. 15, 2024 in Korean Patent Application No. 10-2022-0030870, with English translation, therein, 15 pgs.

(Continued)

*Primary Examiner* — David P Porta
*Assistant Examiner* — Mamadou Faye
(74) *Attorney, Agent, or Firm* — Oblon, McClelland, Maier & Neustadt, L.L.P.

(57) ABSTRACT

The disclosure relates to a device for detecting therapeutic radiation based on an optical disk with solar cells. The radiation detecting device may include at least one optical disk formed of a water-equivalent material, disposed perpendicular to a first direction in which the radiation is incident, and converting the radiation into visible light; a solar cell disposed on one side of the at least one optical disk, converting the visible light into an electrical signal; and a processing module for collecting and processing the electrical signal outputted from the solar cell.

10 Claims, 8 Drawing Sheets

(51) Int. Cl.
*H01J 37/244* (2006.01)
*H10F 19/40* (2025.01)

(52) U.S. Cl.
CPC ...... *H10F 19/40* (2025.01); *A61N 2005/1087* (2013.01); *H01J 2237/24507* (2013.01)

(58) Field of Classification Search
CPC .......... A61N 2005/1087; A61N 5/1071; A61N 5/1075; A61N 2005/1074; A61N 2005/1076; H01J 37/244; H01J 2237/24507; H01L 31/043; H01L 31/042; H01L 31/102
See application file for complete search history.

(56) References Cited

U.S. PATENT DOCUMENTS

| | | | |
|---|---|---|---|
| 2014/0064454 A1* | 3/2014 | Hammond | A61B 6/563 250/336.1 |
| 2016/0327658 A1 | 11/2016 | Shin et al. | |
| 2020/0041662 A1* | 2/2020 | Lu | G01T 1/20185 |
| 2021/0026023 A1* | 1/2021 | Maolinbay | A61N 5/1049 |
| 2022/0028571 A1* | 1/2022 | Downing | G21H 1/02 |

OTHER PUBLICATIONS

Zygmanski, P., et al., Low-cost flexible thin-film detector for medical dosimetry applications, Journal of Applied Clinical Medical Physics (2014) vol. 15, No. 2, pp. 311-326.

\* cited by examiner

DEVICE FOR DETECTING THERAPEUTIC RADIATION BASED ON OPTICAL DISK WITH SOLAR CELLS

CROSS-REFERENCE TO RELATED APPLICATION

This application claims the benefit under 35 U.S.C. § 119 of Korean Patent Application No. 10-2022-0030870 filed on Mar. 11, 2022, in the Korean Intellectual Property Office, the entire disclosure of which is incorporated herein by reference for all purposes.

BACKGROUND

1. Field

The present disclosure relates to a device for detecting therapeutic radiation based on optical disk with solar cells.

2. Description of Related Art

Currently, with the continuous increase in the number of cancer patients, the three main methods of cancer treatment i.e., surgery, chemotherapy, and radiation therapy, have been improved and developed. Among them, radiation therapy is a treatment method that irradiates tumors (e.g., cancer cells) with high-energy radiation (e.g., x-rays, electron beams, etc.) to treat tumors (e.g., destroy cancer cells). Through the rapid development of radiation treatment devices and technologies, the cancer treatment rate is greatly improved, and complications caused by radiation side effects are gradually decreasing.

In particular, particle therapy using high energy protons or carbons among radiation therapies is a therapeutic technique that has the advantage of further reducing side effects compared to conventional X-ray therapy. Such particle therapy uses the physical property called "Bragg peak", which means that when accelerated high-energy particles are incident on a patient's body, delivers most of energy at a specific depth in the body. Subsequently, their energy decreases dramatically. Therefore, the particle therapy has the advantage of very low side effects (caused by radiation) because there is no radiation dose delivered to normal tissues at a depth beyond the Bragg peak.

Recently, the pencil beam scanning technique has been proposed for intensity modulated particle therapy. This technique delivers particle beams to the patient precisely by adjusting the positions of the pencil beam through a combination of the scanning magnets and energy changes. In other words, the dose distribution is formed by a combination of numerous pencil beams. However, there is a problem that the position errors of the pencil beams can cause substantial dose variations. Therefore, verification related to the positions is essential. This is because if the radiation doses are not accurately delivered to tumor (underdose to tumor), the effectiveness of the treatment may decrease rapidly, or the doses beyond acceptable limits are deliver to normal organs (overdose to normal tissue), causing critical side effects.

As such, since the radiation can affect not only tumors but also normal tissues (e.g., cells), it is necessary to verify whether the delivery dose by the pencil beams is accurate before treatment begins (namely, before actually irradiating the patient). For this reason, there is also a growing interest in radiation measurement device in order to ensure the accuracy of the radiation therapy.

Figure 6:
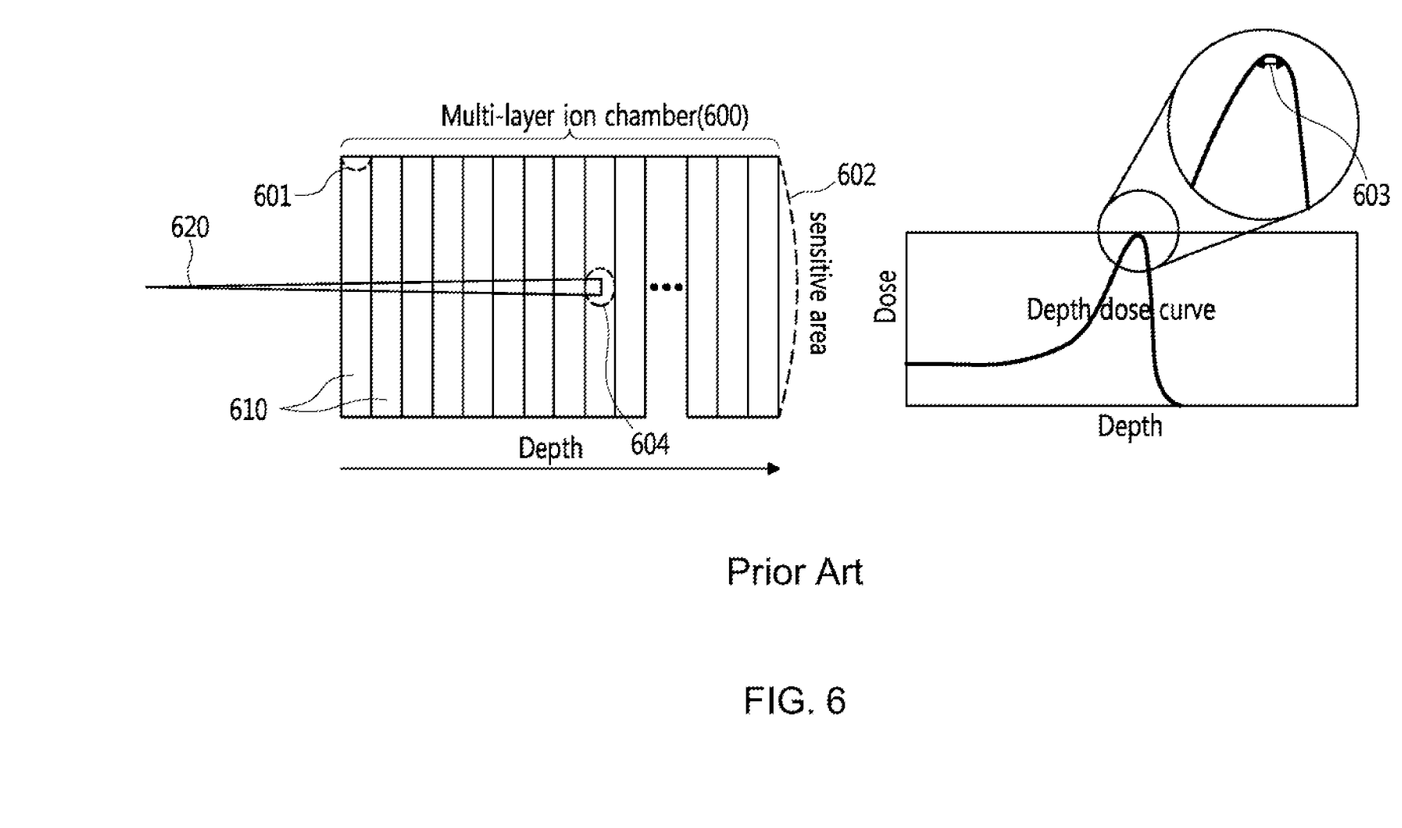
FIG. 6 illustrates a diagram of a method for detecting proton beams using a multi-layer ion chamber according to prior art.

For example, radiation therapy using proton pencil beam scanning may lead to fatal side effect due to the Bragg peak characteristic of proton beam if the proper intensity of proton beams cannot be irradiated at the accurate location. To avoid such side effect, according to prior art, the dose of proton beams 620 is measured using a multi-layer ion chamber (MUG) 600 with multiple ion chambers 610 stacked together, as shown in FIG. 6. Each ion chamber 610 of the multi-layer ion chamber 600 may have a thickness 601 of about 2 mm and a size (i.e., diameter) 602 in a longitudinal direction of about 12 cm. Because the thickness 601 of each ion chamber 610 is greater than a clinically acceptable uncertainty 603 of the depth dose curve of the proton beam 620, i.e., about 1 mm, (that is, low resolution), the multi-layer ion chamber 600 may have an issue in that it is not possible to accurately measure the Bragg peak 604 and the size 602 in the longitudinal direction is limited. In addition, as multiple ion chambers 610 have materials with low similarity to the human body, it may be necessary to correct the measurement results. For this reason, the conventional multi-layer ion chamber 600 may have an issue in that the accuracy of the measurement result may decrease. Further, the multi-layer ion chamber 500 may have an issue that the manufacturing cost is very high.

SUMMARY

To achieve this objective, a device for detecting therapeutic radiation based on optical disk with solar cells according to one or more examples of the present disclosure may include at least one optical disk that is formed of a water-equivalent material, disposed perpendicular to a first direction in which the radiation is incident, and converting the radiation into visible light; a solar cell that is disposed on one side of the at least one optical disk and converts the visible light into an electrical signal; and a processing module that collects and processes the electrical signal outputted from the solar cell.

The optical disk may be formed in shape of a polygon and each side of the optical disk may have a predetermined area. The solar cell may be solid and be respectively disposed on the predetermined area of each side of the optical disk.

The optical disk may be circular. The solar cell may be flexible and may be disposed on a side of the circular optical disk so as to wrap around the circular optical disk.

The optical disk and the solar cell may be each one. The optical disk may be movably disposed in a first direction within a housing by a drive module.

The optical disk and the solar cell may be plural and stacked in the first direction.

The radiation may be a charged particle beam. The optical disk may have a thickness corresponding to a clinically acceptable uncertainty in a depth dose curve of the charged particle beam.

The processing module may include an amplification module for amplifying the electrical signal; a data collecting module for collecting data corresponding to the amplified electrical signal; and a data processing module for analyzing the collected data to calculate a penetration depth of the incident radiation.

The device may further include a display module for displaying a processing result of the data processing module.

The processing module may correct the calculated penetration depth based on at least one of deviation correction, interpolation, or noise filtering for an output of each solar cell.

The device may further include an array of solar cells disposed on a front surface of the at least one optical disk and for detecting a spot position of the radiation.

The array of solar cells may be arranged with solar cells having a predetermined size in multiple rows and columns.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known after understanding of the disclosure of this application may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween.

As used herein, the term "and/or" includes any one and any combination of any two or more of the associated listed items.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

Spatially relative terms such as "above," "upper," "below," and "lower" may be used herein for ease of description to describe one element's relationship to another element as shown in the figures. Such spatially relative terms are intended to encompass different orientations of the device in use or operation in addition to the orientation depicted in the figures. For example, if the device in the figures is turned over, an element described as being "above" or "upper" relative to another element will then be "below" or "lower" relative to the other element. Thus, the term "above" encompasses both the above and below orientations depending on the spatial orientation of the device. The device may also be oriented in other ways (for example, rotated 90 degrees or at other orientations), and the spatially relative terms used herein are to be interpreted accordingly.

The terminology used herein is for describing various examples only, and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

The features of the examples described herein may be combined in various ways as will be apparent after an understanding of the disclosure of this application. Further, although the examples described herein have a variety of configurations, other configurations are possible as will be apparent after an understanding of the disclosure of this application.

The present disclosure addresses the above-mentioned problems of the prior art, and may provide a device for detecting therapeutic radiation based on optical disk with solar cells allows to accurately detect (or measure) the location and/or dose of radiation.

Hereinafter, the configuration of the present disclosure will be described in detail with reference to the accompanying drawings.

Figure 1:
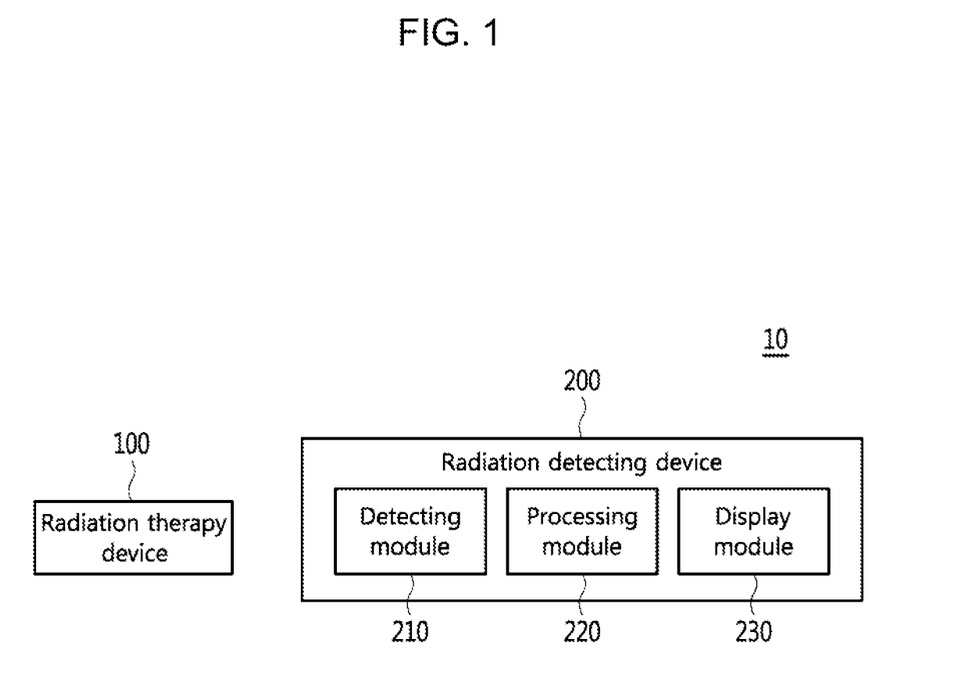
FIG. 1 illustrates a diagram of a radiation therapy system according to one example of the present disclosure.
Figure 2:
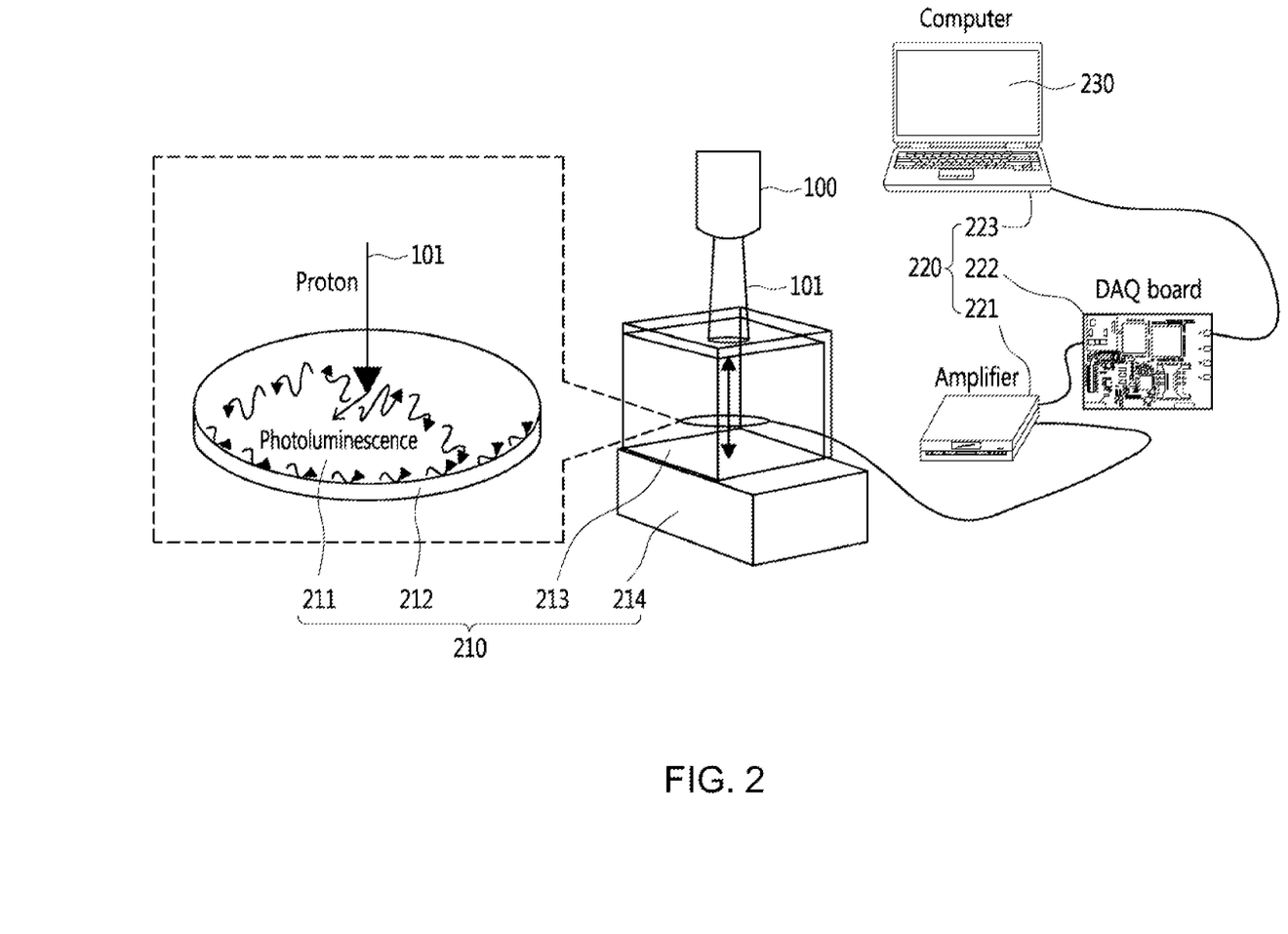
FIG. 2 illustrates a diagram of a single-channel radiation detecting device according to one example of the present disclosure.
Figure 3:
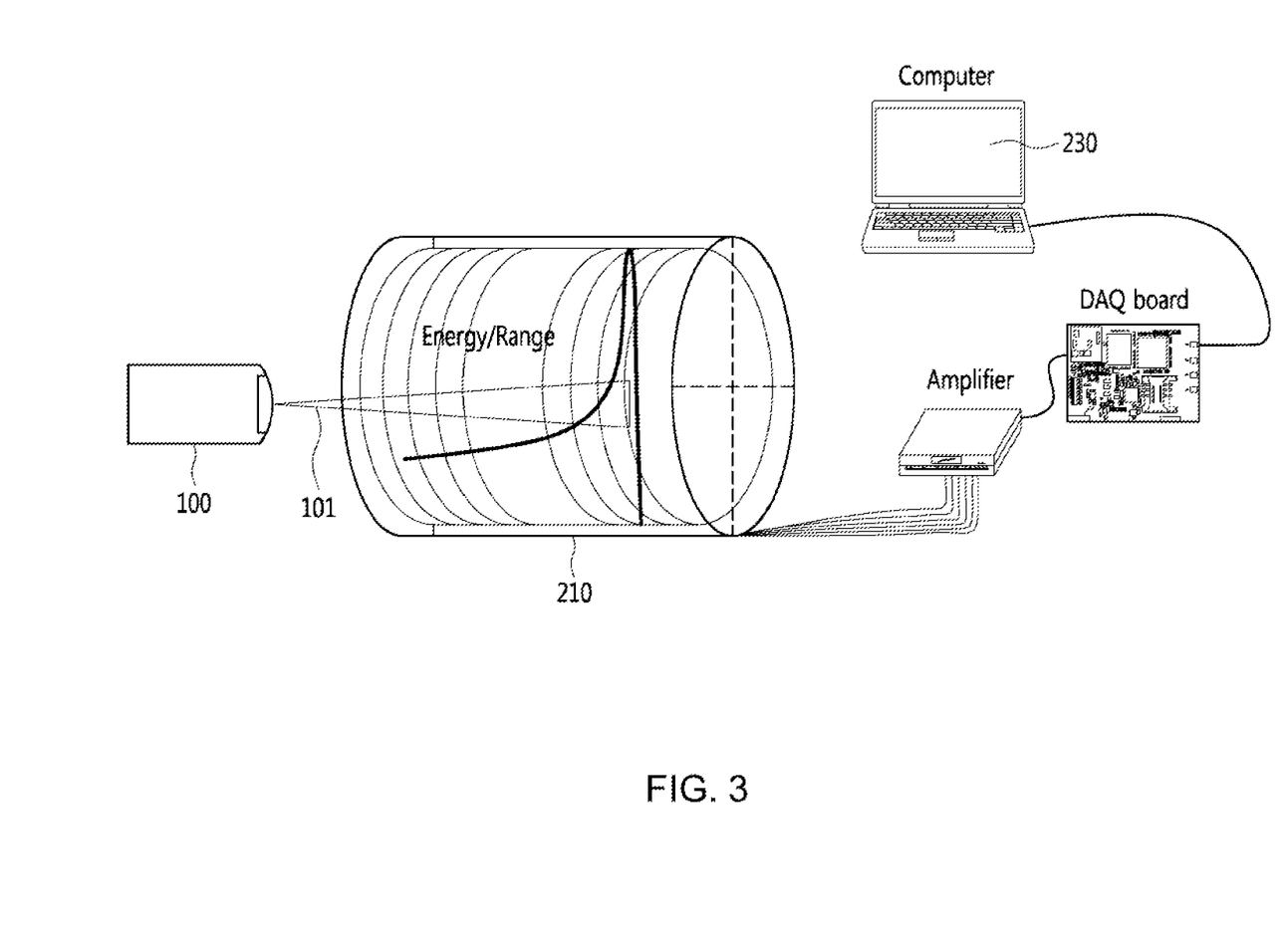
FIG. 3 illustrates a diagram of a multi-channel radiation detecting device according to one example of the present disclosure.
Figure 4A:
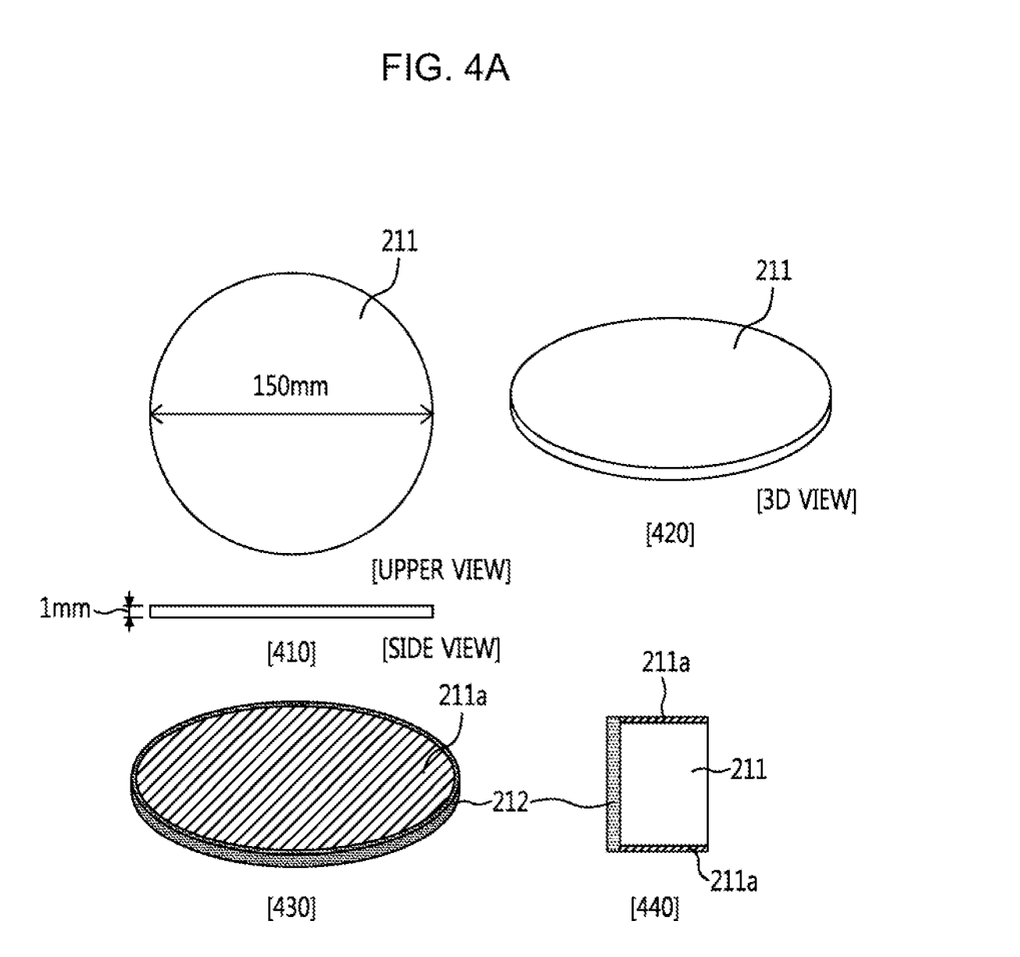
FIG. 4A illustrates a diagram of a combined structure of an optical disk and a solar cell according to one example of the present disclosure.
Figure 4B:
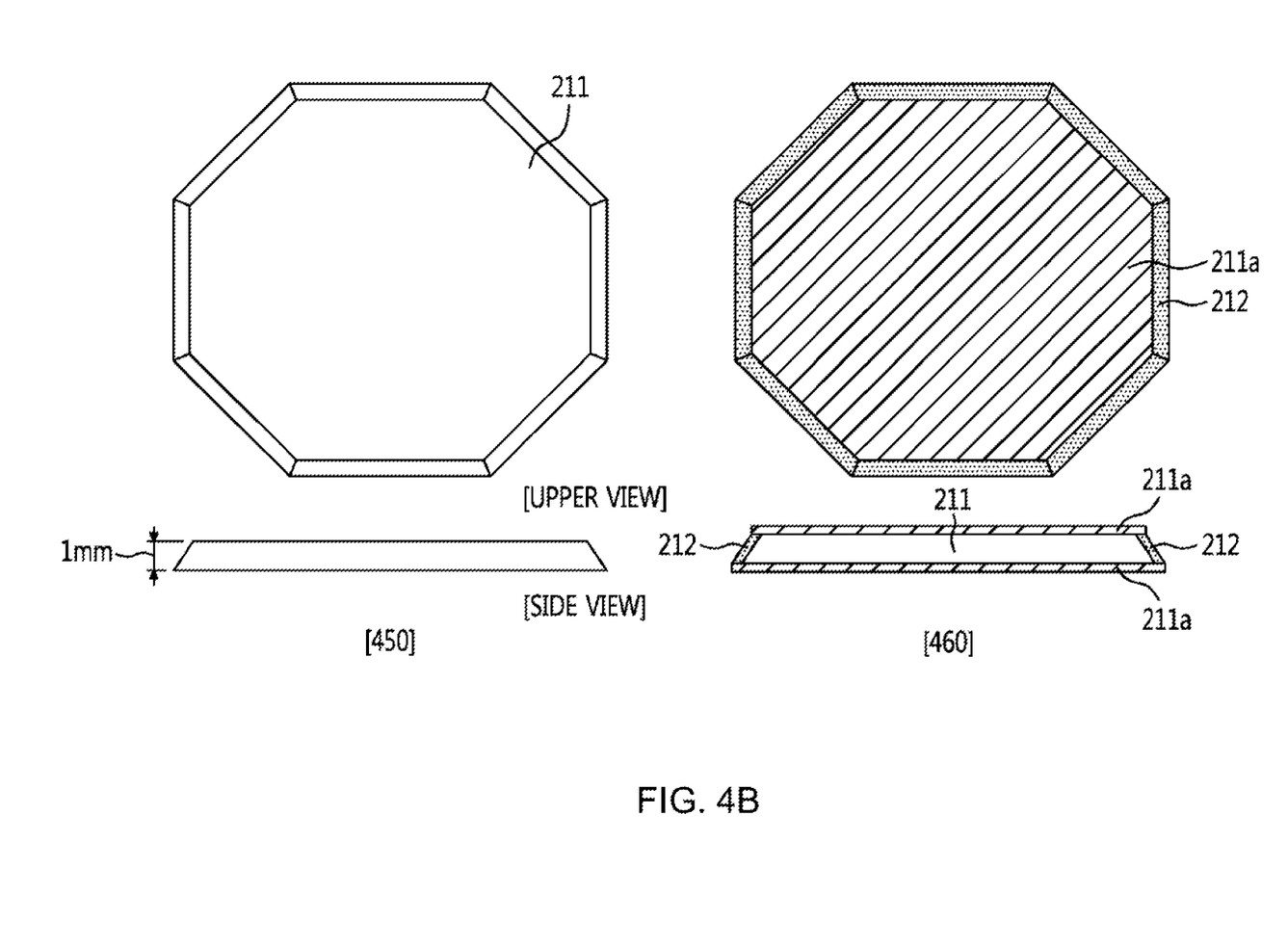
FIG. 4B illustrates a diagram of a combined structure of an optical disk and a solar cell according to another example of the present disclosure.

FIG. 1 illustrates a diagram of a radiation therapy system according to one example of the present disclosure. FIG. 2 illustrates a diagram of a single-channel radiation detecting device according to one example of the present disclosure. FIG. 3 illustrates a diagram of a multi-channel radiation detecting device according to one example of the present disclosure. FIG. 4A illustrates a diagram of a combined structure of an optical disk and a solar cell according to one example of the present disclosure. FIG. 4B illustrates a diagram of a combined structure of an optical disk and a solar cell according to another example of the present disclosure.

Referring to FIGS. 1 to 4B, a radiation therapy system 10 may include a radiation therapy device 100 and a radiation detecting device 200.

According to one example, the radiation therapy device 100 is a device for treating tumors, e.g., cancer cells, and may irradiate a human body with radiation 101 (e.g., x-rays, electron beam, particle beam (e.g., proton beam), carbon beam, etc.). For example, the radiation therapy device 100 may irradiate radiation 101 to a tumor located inside the human body. The radiation 101 may be irradiated in the form of a pencil beam.

According to one example, the radiation detecting device 200 is a device for confirming (verifying) whether the radiation therapy device 100 is able to accurately irradiate radiation to a tumor located inside the human body before treating the tumor using the radiation therapy device 100. For example, the radiation detecting device 200 may verify (measure) a penetration depth (or dose) of the radiation 101 outputted from the radiation therapy device 100.

The radiation detecting device 200 according to one example may include a detecting module 210, a processing module 220, and a display module 230. The detecting module 210 allows to detect radiation outputted from the radiation therapy device 100. For example, the detecting module 210 may detect the radiation 101 using at least one conversion module (e.g., including an optical disk 211 and a solar cell 212).

First, if the detecting module 210 includes a single conversion module (hereinafter referred to as a single channel), the detecting module 210 may detect the radiation 101 by moving the conversion module in a first direction within a housing 213 (e.g., water phantom) via the drive module 214, as shown in FIG. 2. In other words, the detecting module 210 detects the radiation 101 by moving the conversion module along an optical axis of the radiation 101. In detail, the detecting module 210 may detect the radiation 101 via the optical disk 211 and the solar cell 212 up to the penetration depth of the radiation 101, but if the penetration depth is exceeded, the radiation 101 may not be detected via the optical disk 211 and the solar cell 212. This allows the radiation detecting device 200 to move the conversion module to determine (or measure) the penetration depth of the radiation 101. Accordingly, the radiation detecting device 200 that supports a single channel allows to finely move the conversion module and accurately determine the penetration depth of the radiation (i.e., the Bragg peak).

On the other hand, if the detecting module 210 includes a plurality of conversion modules (hereinafter referred to as a multi-channel), the detecting module 210 may detect the radiation 101 via a plurality of conversion modules stacked in a first direction, as shown in FIG. 3. In detail, when the radiation 101 is sent toward the detecting module 210, the conversion modules located within the depth at which the radiation 101 is penetrated will output a detection signal, and the optical disk 211 and solar cell 212 located outside the penetration depth will not output the detection signal. This allows the radiation detecting device 200 to determine the penetration depth of the radiation 201. In this case, the thickness (resolution) of the optical disk 211 constituting the conversion module has a size (about 1 mm) corresponding to (or similar to) a clinically acceptable uncertainty. Accordingly, the radiation detecting device 200 supporting a multi-channel may detect the penetration depth of radiation (i.e., the Bragg peak) more accurately than a conventional multi-ion chamber.

Meanwhile, the optical disk 211 is formed of a human body-like material (e.g., water-equivalent material) and converts the radiation 101 into visible light. The solar cell 212 may convert visible light into an electrical signal. The optical disk 211 may be disposed perpendicular to a first direction in which the radiation 101 is incident.

The optical disk 211 may be formed in a circular or polygonal shape, and a solar cell may be disposed on one side thereof. For example, the optical disk 211 may be formed in a circular shape, as shown by reference numeral 410 of FIG. 4A. The optical disk 211 may have a thickness (e.g., about 1 mm) corresponding to a clinically acceptable uncertainty in the depth dose curve of the charged particle beam, and a predetermined diameter (e.g., 150 mm), but is not limited thereto. To the side of the optical disk 211, a solar cell 212 may be attached, as shown by reference numeral 420 in FIG. 4A. In this case, the solar cell 212 is formed of a flexible material and may be attached (or disposed) to the side of the optical disk 211 so as to wrap around the optical disk 211, as shown by reference numerals 430, 440 in the drawing. The solar cell 212 may have a length corresponding to a circumference of the optical disk 211. According to another example, the optical disk 211 may have grooves (not shown) formed on the side surface thereof, and the solar cell 212 may be disposed in the groove of the optical disk 211.

According to another example, the optical disk 211 may be formed in a polygon (e.g., an octagon), as shown by reference numeral 450, although not limited thereto. The optical disk 211 may have a predetermined thickness (e.g., about 1 mm) and a predetermined length (e.g., 140 mm). In addition, the optical disk 211 may have sides with 'edge design', which means each side of the optical disk is inclined at a certain angle rather than at right angle. This is to increase the attachment area of the solar cell 212, in short, as each side of the optical disk is formed at a certain angle rather than a right angle, the area to which the solar cell 212 is attached may be increased compared to when they are formed at a right angle. The solar cells 212 may be disposed on each side of the polygonal optical disk 211, as shown by reference numeral 460 in FIG. 4B. The solar cell 212 disposed on side surface of each side of the optical disk 211 may be formed from a solid material or a flexible material. The solar cells 212 disposed on each side of the optical disk 211 may be connected in series. The structure shown in FIG. 4B is useful when it is difficult to make the thickness of the solar cells (e.g., solar cells of solid material) equal to or less than the thickness of the optical disk (e.g., 1 mm).

On the other hand, a reflective film 211a may be attached to the front and rear surfaces of the optical disks 211 of FIGS. 4A and 4B. The reflective film 211a may be formed of a material (e.g., formed by applying a reflective material (e.g., silver, etc.) to a thin film of PET film) allowing not to affect the transmission of radiation.

The reflective film 211a may be formed from a material (e.g., formed by applying a reflective material (e.g., silver, etc.) to a thin film of PET film) so as not to affect the transmission of radiation. As the reflective film 211a covers both the front and rear of the optical disk 211, the visible light generated on the optical disk 211 by the radiation is not able to escape to the outside through the front and/or rear of the optical disk 211, and may be delivered (directed) to the side surface on which the solar cell 212 is disposed.

According to examples of the present disclosure, as the solar cell 212 is disposed on the side of the optical disk 211, as shown in FIGS. 4A and 4B, the solar cell 212 may not interfere with the transmission of radiation, such as in the example where the solar cell 212 is disposed on the front or rear of the optical disk 211, thereby improving the accuracy of radiation detection.

According one example, the processing module 220 may collect and process an electrical signal outputted from solar cells of the detecting module 210. For example, the processing module 220 may detect a penetration depth and/or location of radiation based on the collected electrical signal. The processing module may include an amplification module 221 that is electrically connected to the solar cell and amplifies the collected electrical signal, a data collecting module 222 that collects data corresponding to the amplified electrical signal, and a data processing module 223 that analyzes the collected data to calculate the penetration depth and/or location of the radiation.

According to one example, the processing module 220 may correct the above calculated penetration depth by performing at least one of deviation correction, interpolation, or noise filtering for the output of each solar cell 212. For example, the processing module 220 corrects the output deviation of the optical disk/solar cell constituting each channel if the radiation detecting device 200 supports a multi-channel, as shown in FIG. 3. In addition, in the case of a multi-channel radiation detecting device, in the processing module 220, signals are detected at regular intervals (thickness of the optical disk). In this case, the processing module 220 may restore a signal between each interval using interpolation. In addition, the processing module 220 may support a filtering function to remove noise included in a signal outputted from the solar cell 212 (e.g., a low pass filter or a band pass filter).

The display module 230 may display a processing result of the processing module 220. For example, the display module 230 may display a penetration depth and/or a location. According to one example, the display module 230 may display a dose distribution graph.

According to one example, some components of the processing module 220 (e.g., a data processing module 223) and the display module 230 may be included in one electronic device (e.g., a desktop PC or a laptop).

Figure 5A:
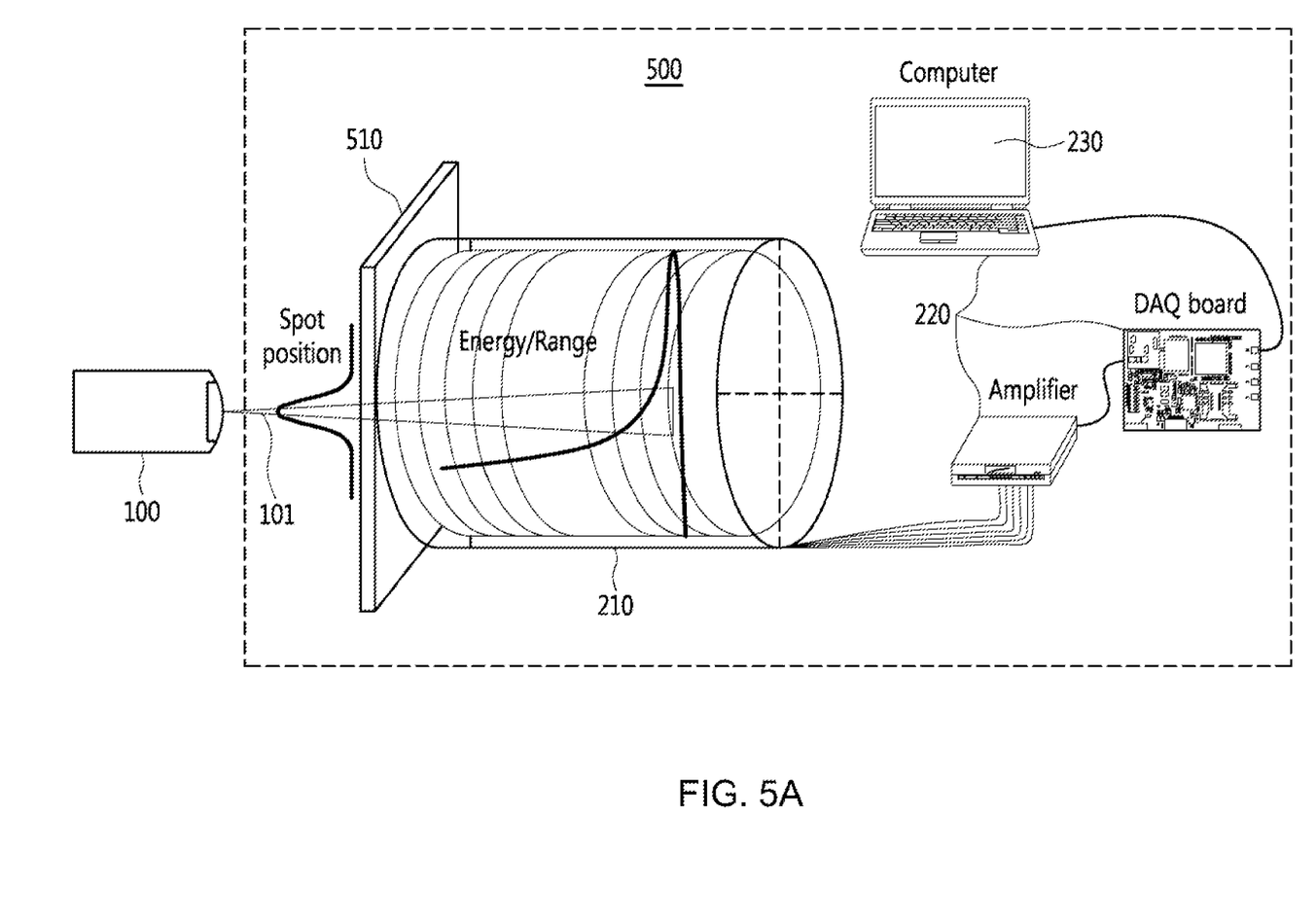
FIG. 5A illustrates a diagram of a radiation detecting device according to another example of the present disclosure.
Figure 5B:
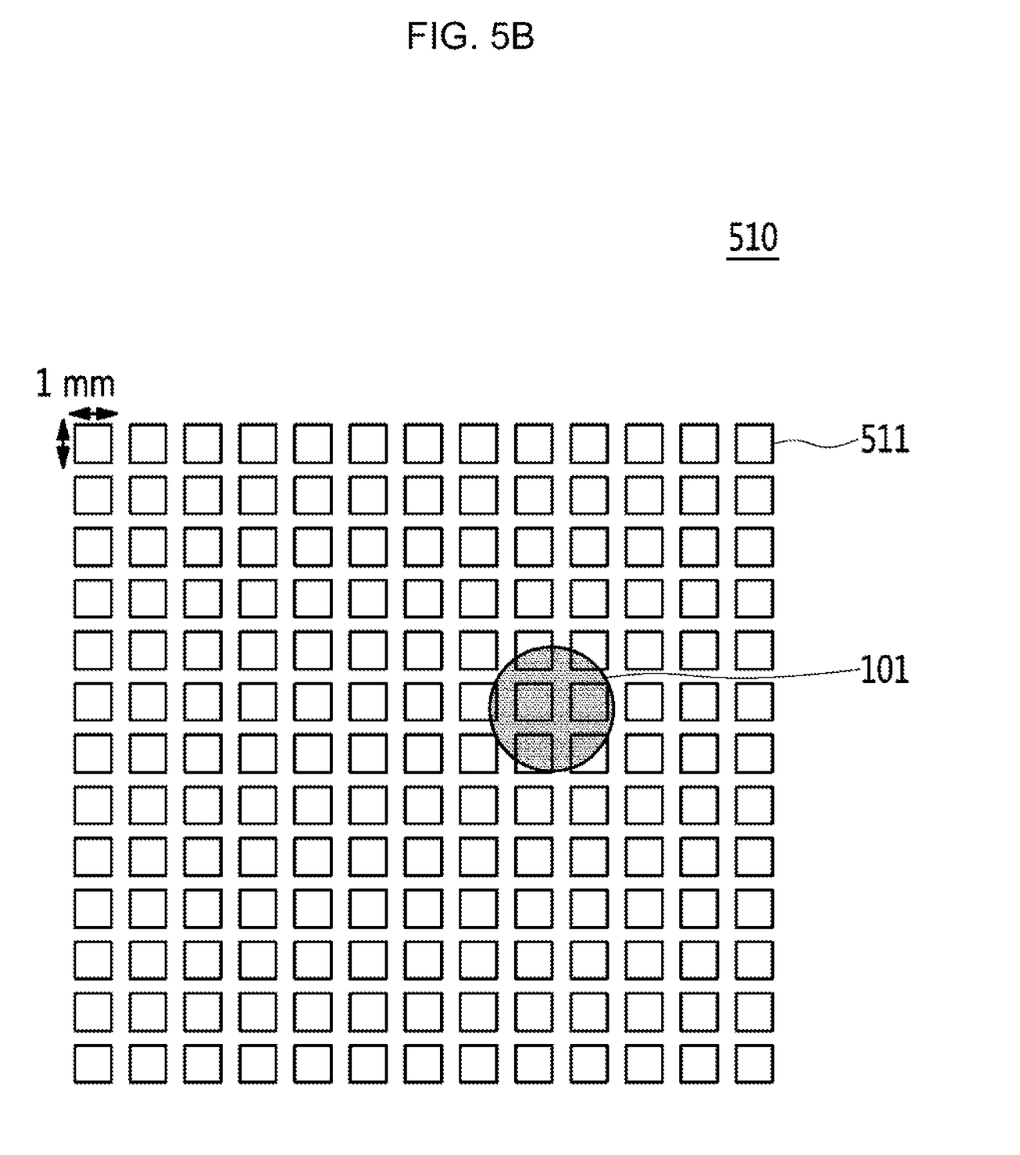
FIG. 5B illustrates a diagram of an array of solar cells included in the radiation detecting device of FIG. 5A.

FIG. 5A illustrates a diagram of a radiation detecting device according to another example of the present disclosure. FIG. 5B illustrates a diagram of an array of solar cells included in the radiation detecting device of FIG. 5A.

Referring to FIGS. 5A and 5B, a radiation detecting device 500 according to another example of the present disclosure may determine the penetration depth and position (or spot position) of the radiation 101 outputted from the radiation therapy device 100. The radiation detecting device 500 may include a detecting module 210, a processing module 220, and a display module 230 in order to detect the penetration depth of the radiation 101, and may further include an array of solar cells 510 on the front surface of the detecting module 210 in order to detect the location of the radiation 101.

In the array of solar cells 510, solar cells 511 with a predetermined size (e.g., 1 mm×1 mm) may be arranged in multiple rows and columns, as shown in FIG. 5B. Among the solar cells arranged in multiple rows and columns, solar cells located in a region to which the radiation 101 is irradiated may output an electrical signal. In other words, the radiation detecting device 500 may determine the location (spot position) where radiation is irradiated through the location of the solar cell that outputs an electrical signal among the solar cells included in the array of solar cells 510.

The radiation detecting device 500 of FIG. 5A described above allows to measure the location and penetration depth of radiation at once, reduce measurement time and setup time, thereby improving the efficiency of verifying the radiation therapy device. This allows to improve the quality of patient treatment.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A device for detecting therapeutic radiation, comprising:
    a single optical disk that is formed of a water-equivalent material, disposed perpendicular to a first direction in which the radiation is incident, and converting the radiation into visible light;
    a single solar cell that is disposed on one side of the optical disk and converts the visible light into an electrical signal; and
    processing circuitry configured to collect and process the electrical signal outputted from the solar cell,
    wherein the optical disk is movably disposed in a first direction within a housing by a drive module.

2. The device of claim 1, wherein the optical disk is formed in shape of a polygon and each side of the optical disk has a predetermined area, and
    wherein the solar cell is solid and is respectively disposed on the predetermined area of each side of the optical disk.

3. The device of claim 1, wherein the optical disk is circular, and
    wherein the solar cell is flexible and is disposed on a side of the circular optical disk so as to wrap around the circular optical disk.

4. The device of claim 1, wherein the radiation is a charged particle beam, and
    wherein the optical disk has a thickness corresponding to a clinically acceptable uncertainty in a depth dose curve of the charged particle beam.

5. The device of claim 1, wherein the processing circuitry is further configured to:
    amplify the electrical signal output from the solar cell,
    collect data corresponding to the amplified electrical signal; and
    analyze the collected data to calculate a penetration depth of the incident radiation.

6. The device of claim 5, further comprising a display displaying a processing result of the processing circuitry.

7. The device of claim 5, wherein the processing circuitry is further configured to correct the calculated penetration depth based on at least one of deviation correction, interpolation, or noise filtering for an output of the solar cell.

8. A device for detecting therapeutic radiation, comprising:
- an optical disk that is formed of a water-equivalent material, disposed perpendicular to a first direction in which the radiation is incident, and converting the radiation into visible light;
- an array of solar cells disposed on one side of the optical disk, the array of solar cells converting the visible light into an electrical signal; and
- processing circuitry configured to collect and process the electrical signal outputted from the array of solar cells, wherein the array of solar cells is disposed on a front surface of the optical disk and detects a spot position of the radiation.

9. The device of claim 8, wherein the array of solar cells is arranged with solar cells having a predetermined size in multiple rows and columns.

10. A device for detecting therapeutic radiation, comprising:
- an optical disk that is formed of a water-equivalent material, disposed perpendicular to a first direction in which the radiation is incident, and converting the radiation into visible light;
- a solar cell that is disposed on one side of the optical disk and converts the visible light into an electrical signal; and
- processing circuitry configured to collect and process the electrical signal outputted from the solar cell,
- wherein the optical disk is circular, and
- wherein the solar cell is flexible and is disposed on a side of the circular optical disk so as to wrap around the circular optical disk.

* * * * *